United States Patent
Webb et al.

(10) Patent No.: US 6,652,878 B2
(45) Date of Patent: *Nov. 25, 2003

(54) CELL TRANSFECTION APPARATUS AND METHODS FOR MAKING AND USING THE CELL TRANSFECTION APPARATUS

(75) Inventors: Brian L. Webb, Painted Post, NY (US); Bernice I. Feuer, Berkeley Heights, NJ (US); Laurent A. G. Picard, Corning, NY (US)

(73) Assignee: Corning Incorporated, Corning, NY (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/155,098

(22) Filed: May 24, 2002

(65) Prior Publication Data

US 2003/0092181 A1 May 15, 2003

Related U.S. Application Data

(63) Continuation of application No. 09/962,054, filed on Sep. 24, 2001.
(51) Int. Cl.[7] .......................... A61K 9/127; C12M 3/00; G03C 5/00; C12Q 1/68
(52) U.S. Cl. .......................... 424/450; 430/326; 435/6; 435/285.1; 435/458
(58) Field of Search ........................ 435/6, 285.1, 458; 424/450; 430/326

(56) References Cited

U.S. PATENT DOCUMENTS

| | | | |
|---|---|---|---|
| 5,654,185 A | | 8/1997 | Palsson |
| 5,804,431 A | | 9/1998 | Palsson |
| 5,811,274 A | | 9/1998 | Palsson |
| 6,022,700 A | | 2/2000 | Monks et al. |

FOREIGN PATENT DOCUMENTS

| | | |
|---|---|---|
| WO | WO 99/00520 A1 | 1/1999 |
| WO | WO 99/14376 A1 | 3/1999 |
| WO | WO 99/55826 A1 | 11/1999 |
| WO | WO 99/55886 A1 | 11/1999 |

OTHER PUBLICATIONS

S. Drmanac et al. "Processing of cDNA and Genomic Kilobase–Size Clones for Massive Screening, Mapping and Sequencing by Hybridization", 7 pages, BioTechniques, vol. 17, No. 2 (1994).

J. Ziauddin et al. "Microarrays of Cells Expressing Defined cDNAs", Nature 411:107–110 (May 3, 2001).

*Primary Examiner*—James Ketter
(74) *Attorney, Agent, or Firm*—William J. Tucker

(57) ABSTRACT

A cell transfection apparatus and methods for making and using the cell transfection apparatus are described. The cell transfection apparatus has a surface on which there is printed at different locations one or more foreign biomolecules (e.g., DNA, RNA, oligonucleotides, nucleotides). The foreign biomolecules can be printed at the same time. The surface is then covered with a transfection reagent which is incubated and removed from the surface before cells in a cell growth media are placed on the surface. The surface is configured such that the cells which become transfected with one or more foreign biomolecules are segregated from the cells which fail to become transfected with one or more foreign biomolecules. There are disclosed two embodiments of the cell transfection apparatus.

40 Claims, 11 Drawing Sheets

CELL TRANSFECTION APPARATUS AND METHODS FOR MAKING AND USING THE CELL TRANSFECTION APPARATUS

This application is a Continuation of prior application Ser. No. 09/962,054 filed on Sep. 24, 2001, now pending.

BACKGROUND OF THE INVENTION

1. Field of the Invention

The present invention relates in general to the biotechnology field and, in particular, to an apparatus and method that can be used to effectively produce an array of transfected cells.

2. Description of Related Art

The recent completion of the Human Genome Project means that researchers are going to be asked to study the functions of thousands of known genes and unknown genes in DNA sequences. As such, the researchers are going to need tools that can enable them to effectively and expeditiously study the functions of these genes and the proteins encoded by these genes.

Traditional tools that are used by researchers to perform these studies are not effective, because they make it hard for the researchers to produce an array of transfected cells. The transfection of cells is the introduction of one or more exogenous genes into target cells. Transfected cells produce the proteins encoded by the exogenous genes. The study of these proteins has diverse applications in a wide variety of fields including, for example, the pharmaceutical field, the medical field and the agricultural field. An example of a traditional cell transfection apparatus is briefly discussed below with respect to FIG. 1.

Referring to FIG. 1 (PRIOR ART), there is illustrated a perspective view of a traditional cell transfection apparatus 100. Basically, the traditional cell transfection apparatus 100 is a slide 102 on which a robotic arrayer prints a plasmid DNA 104 dissolved in an aqueous gelatin solution. The slide 102 is dried and the printed array of plasmid DNA 104 is covered with a lipid transfection reagent 106. Alternatively, the lipid transfection reagent 106 can be added to the plasmid DNA 104 before the DNA is printed. After removal of the lipid transfection reagent 106, the slide 102 is placed in a culture dish 108 and covered with cells in a growth media 110. The arrayed cells become transfected in one to two days after which the researchers can study the proteins encoded by the plasmid DNA 104. For a more detailed discussion about the traditional cell transfection apparatus 100 reference is made to an article by J. Ziauddin and D. M Sabatini, "Microarrays of Cells Expressing Defined cDNAs" Nature 411, 107–110 (May 3, 2001). This article is hereby incorporated by reference herein.

Unfortunately, there are many drawbacks associated with the traditional cell transfection apparatus 100. First, the cells 110 attach and grow over the total surface area of the slide 102 covering the printed plasmid DNA 104 and the areas between the spots of plasmid DNA 104. As such, the transfected cells can be located only if transfection occurs and the plasmid DNA 104 is engineered to carry a marker or protein tag (e.g., green fluorescent protein, HA, FLAG), radiolabel or an antibiotic resistance protein. Secondly, the robotic arrayer prints the plasmid DNA 104 onto the. slide 102 one spot at a time which is not only very time consuming but also slows down the production rate. Accordingly, there is a need for a cell transfection apparatus that is designed to address the aforementioned problems and other problems associated with the traditional cell transfection apparatus 100. This need and other needs are addressed by the cell transfection apparatus and methods of the present invention.

BRIEF DESCRIPTION OF THE INVENTION

The present invention includes a cell transfection apparatus and methods for making and using the cell transfection apparatus. The cell transfection apparatus has a surface on which there is printed at different locations one or more foreign biomolecules (e.g., DNA, RNA, oligonucleotides, nucleotides). The foreign biomolecules can be printed at the same time. The surface is then covered with a transfection reagent which is incubated and removed from the surface before cells in a cell growth media are placed on the surface. The surface is configured such that the cells which become transfected with one or more foreign biomolecules are segregated from the cells which fail to become transfected with one or more foreign biomolecules. There are two embodiments of the cell transfection apparatus described herein.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 2–10, there are disclosed two embodiments of a cell transfection apparatus and preferred methods for making and using the cell transfection apparatus. Basically, the cell transfection apparatus has a surface on which there is printed at different locations one or more foreign biomolecules (e.g., DNA, RNA, oligonucleotides, nucleotides). The foreign biomolecules can be printed at the same time. The surface is then covered with a transfection reagent which is incubated and removed from the surface before cells in a cell growth media are placed on the surface. The surface is configured such that the cells which become transfected with one or more foreign biomolecules are segregated from the cells which fail to become transfected with one or more foreign biomolecules. How the surface is configured to segregate the transfected cells from the non-transfected cells is described below with respect to two embodiments of the cell transfection apparatus. The first embodiment is referred to as a cell transfection microplatform apparatus 200 (see FIGS. 2–5). And, the second embodiment is referred to as a cell transfection plate 600 (see FIGS. 6–9).

Figure 2A:
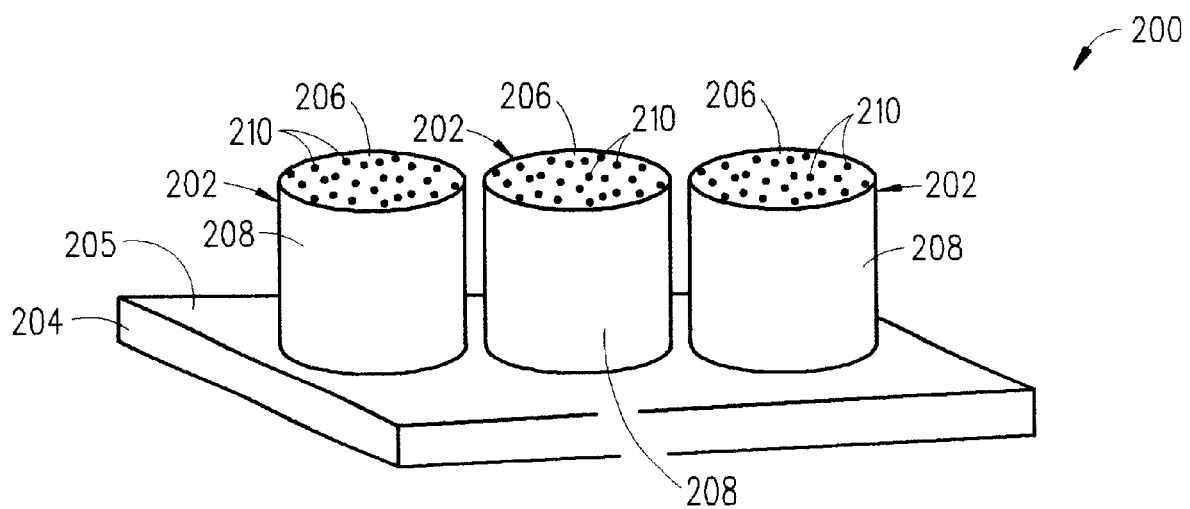
FIGS. 2A–2C illustrates a first embodiment of a cell transfection apparatus in accordance with the present invention.
Figure 2B:
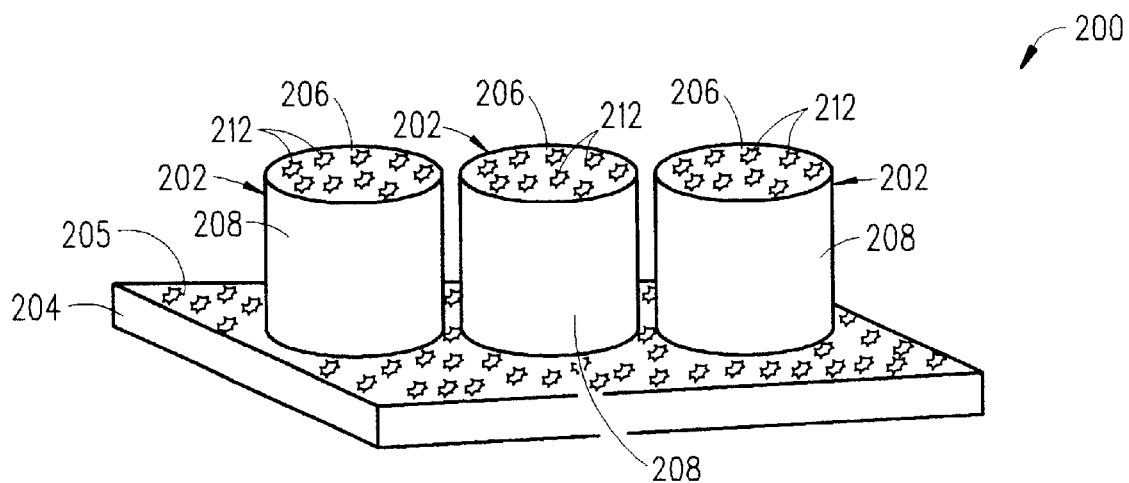
Figure 2C:
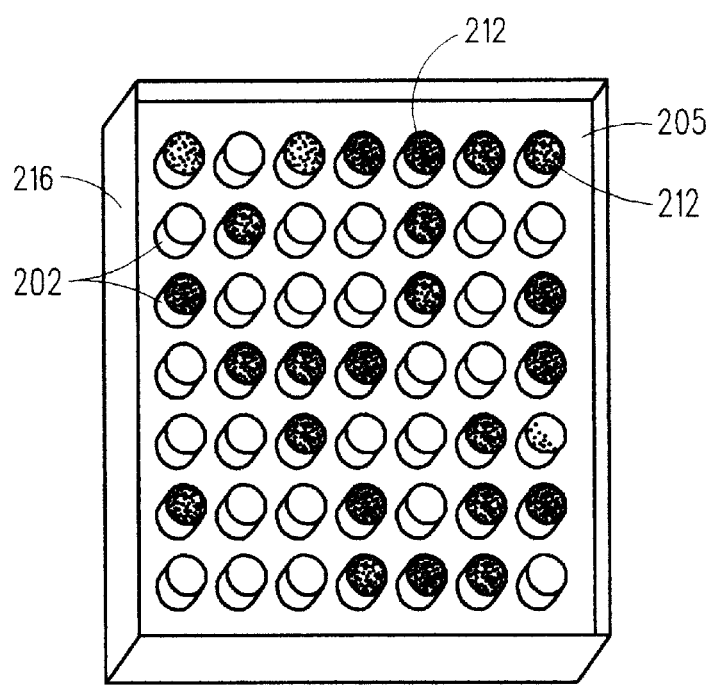

Referring to FIGS. 2A–2C, there are illustrated different views of the cell transfection microplatform apparatus 200 at different stages during the transfection process. The cell transfection microplatform apparatus 200 includes multiple microplatforms 202 (only three shown) extending from a support structure 204. Each microplatform 202 has one or more side surfaces 208 and a top surface 206 distally located from a top surface 205 of the support structure 204. The microplatforms 202 shown have the shape of a circle but it should be understood that the microplatforms 202 can have a wide-variety of shapes including, for example, squares, rectangles, triangles, ovals and polygons.

Figure 1:
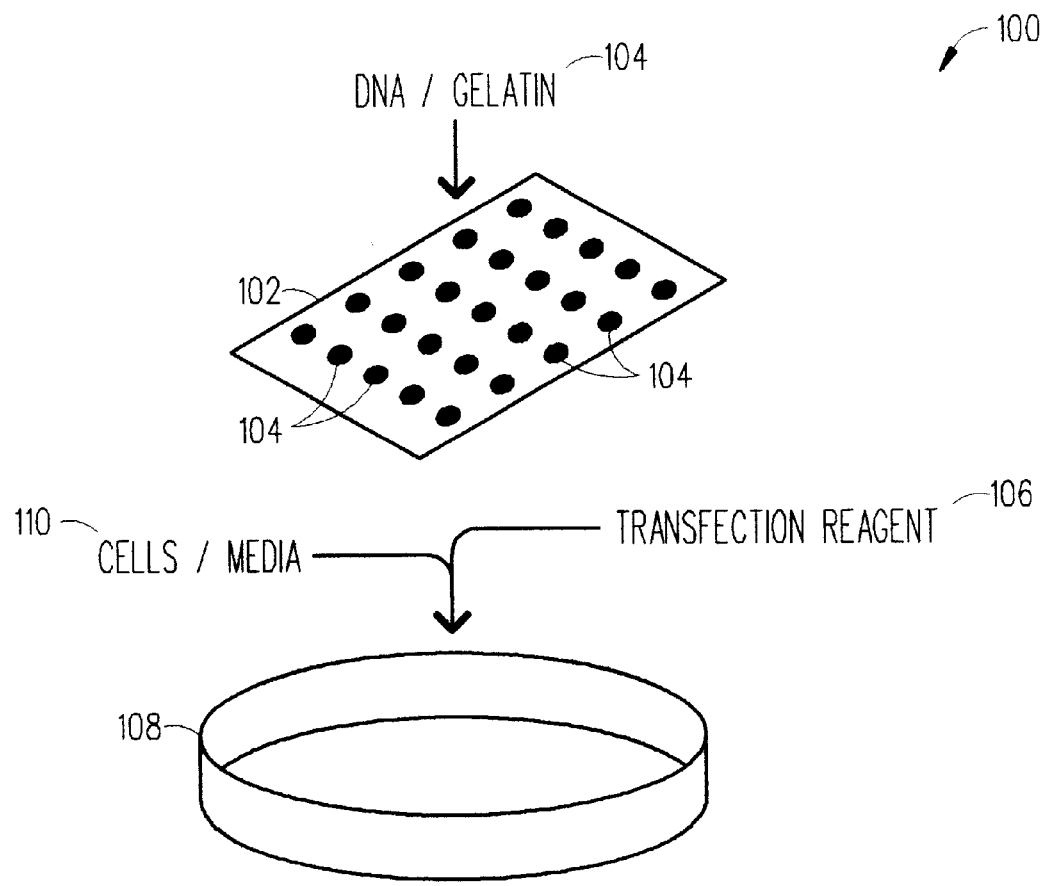
FIG. 1 (PRIOR ART) illustrates a perspective view of a traditional cell transfection apparatus.

Referring to FIG. 2A, there is illustrated a partial perspective side view of the cell transfection microplatform apparatus 200. At this stage, the microplatforms 202 (only three shown) have one or more foreign biomolecules 210 (e.g., DNA, RNA, oligonucleotides, nucleotides) printed on the top surfaces 206. In particular, all of the foreign biomolecules 210 can be printed at one time onto the top surfaces 206. To accomplish this, the cell transfection microplatform apparatus 200 is aligned over and then lowered into a redrawn reservoir (not shown) such that each microplatform 202 is inserted into a corresponding well of the redrawn reservoir. The wells of the redrawn reservoir contain the same or different foreign biomolecules 210. Thereafter, the cell transfection microplatform apparatus 200 is removed from the redrawn reservoir and the top surfaces 206 retain a portion of the foreign biomolecules 210. This process for printing at the same time a high density array of foreign biomolecules 210 is a marked improvement over the prior art which used a robotic arrayer to print the foreign biomolecules one at a time onto the traditional cell transfection apparatus 100 (see FIG. 1).

Referring to FIG. 2B, there is illustrated a partial perspective side view of the cell transfection microplatform apparatus 200. At this stage, the microplatforms 202 have a transfection reagent (e.g., Effectine, Lipofectamine, calcium phosphate, DEAE-dextran, cationic lipids) (not shown in FIG. 2B) added onto the printed foreign biomolecules 210. The lipid-based transfection reagent condenses and coats the printed foreign biomolecules 210 which are immobilized on the top surfaces 206 with lipids. After a short incubation, the transfection reagent is removed. Alternatively, the transfection reagent can be mixed with the foreign biomolecules 210 and printed onto the cell transfection microplatform apparatus 200.

The desired cells 212 (e.g., HEK 293, COS-7, CHO) and cell growth media are dispensed onto the cell transfection microplatform apparatus 200. The cells 212 settle and attach to the flat surfaces including, the top surfaces 206 of the microplatforms 202 and the top surface 205 of the support structure 204. The cells 212 are added at a high enough concentration so that a sufficient number of cells 212 (e.g., 50–150 cells) settle and attach to each top surface 206. The side surfaces 208 and possibly the top surface 205 of the support structure 204 could be treated with a non-binding compound to help prevent cell attachment at these locations. As such, the cells 212 (not necessarily all of the cells 212) on the top surfaces 206 of the microplatforms 202 become transfected with one or more foreign biomolecules while the spatially segregated cells 212 located on the top surface 205 of the support structure 204 fail to become transfected with one or more foreign biomolecules 210. This type of transfection process is known as a reverse transfection process.

To enable the addition of the cells 212 and the cell growth media, the cell transfection microplatform apparatus 200 could have a skirt 216 located around the perimeter which extends above the top surfaces 206 of the microplatforms 202 (see FIG. 2C). Alternatively, the cell transfection microplatform apparatus 200 could be placed into a separate cell growth chamber (not shown).

Referring to FIG. 2C, there is illustrated a top view of the cell transfection microplatform apparatus 200 that has been used to generate a transfection cell array. To generate the transfection cell array, the cells 212 attached to each microplatform 202 become transfected by the foreign biomolecule (s) 210 printed on the respective microplatform and as such express the protein(s) encoded by the printed foreign biomolecule(s) 210. In other words, each microplatform 202 supports the growth of a group of transfected cells 212 that express one or more proteins. As such, the cell transfection microplatform apparatus 200 can be used to generate an array of transfected cells 212 which express as many different proteins as there are different printed foreign biomolecules 210. To confirm the expression of the foreign biomolecules 210 within each cell cluster, a DNA plasmid construct may be used that produces a fusion protein between the protein of interest and a Green Fluorescent Protein (GFP) or other tags e.g. HA and FLAG. It should be understood that the cell transfection microplatform apparatus 200 can have any number of microplatforms 202 and is not limited to any specific dimensions and configurations. For example, the cell transfection microplatform apparatus 22 can have 1024 microplatforms 202 (32×32 array) each of which are 50–150 microns in diameter and 200 microns tall.

Figure 3A:
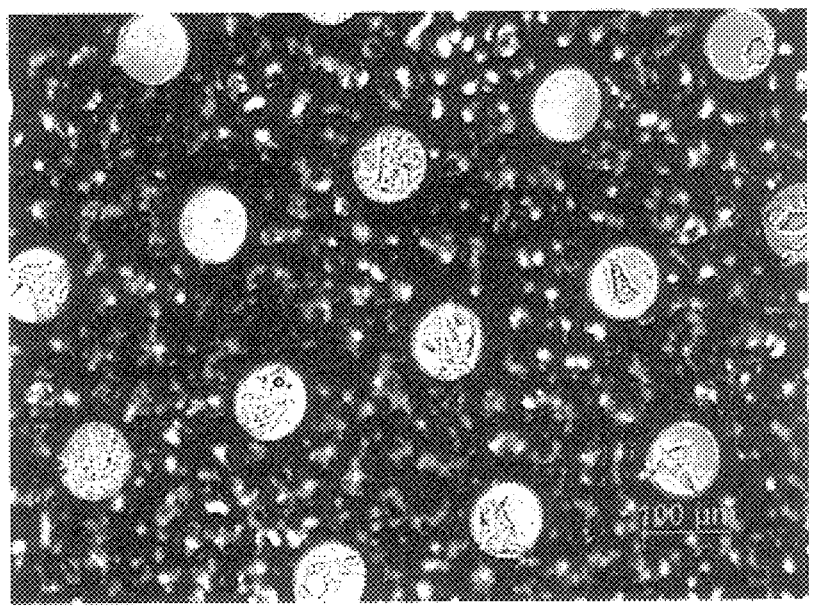
FIGS. 3A–3B are two photographs of HEK 293 cells attached to microplatforms of the first embodiment of the cell transfection apparatus shown in FIG. 2.
Figure 3B:
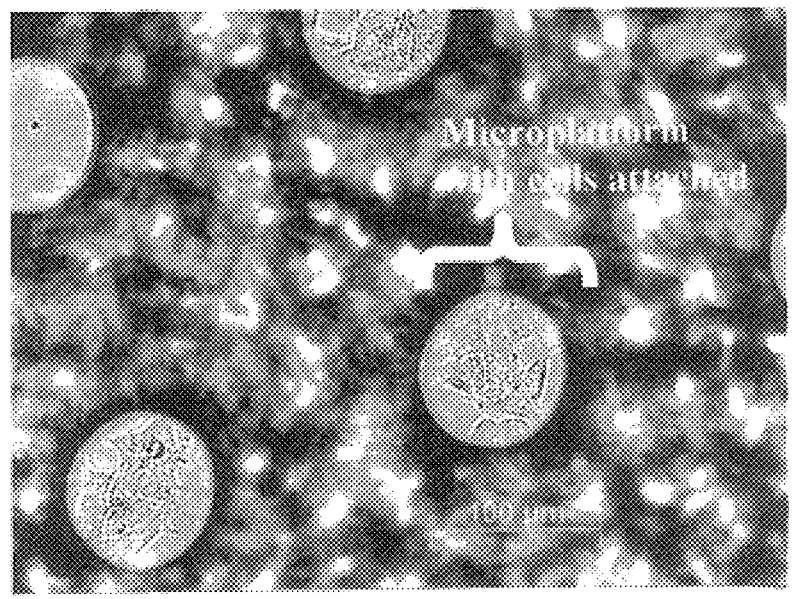

Referring to FIGS. 3A–3B, there are illustrated two photographs of HEK 293 cells 212 attached to the microplatforms 202 of the cell transfection microplatform apparatus 200. In this example, HEK 293 cells 212 were trypsinized, suspended in a cell growth media, and allowed to attach on top of the cell transfection microplatform apparatus 200 for about 24 hours. After which, the HEK 293 cells 212 had attached and started to grow on the top surfaces 206 of the microplatforms 202. Compare the 10× photograph of the HEK 293 cells 212 shown in FIG. 3A to the 20× photograph of the HEK 293 cells 212 shown in FIG. 3B.

Figure 3C:
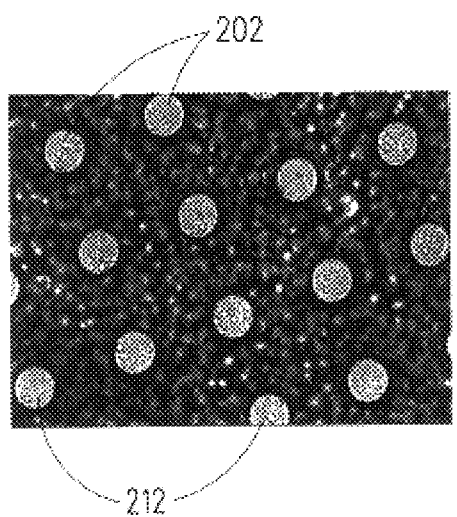
FIGS. 3C–3D are two photographs one of attached HEK 293 cells and another of transfected HEK 293 cells on the microplatforms of the first embodiment of the cell transfection apparatus shown in FIG. 2.
Figure 3D:
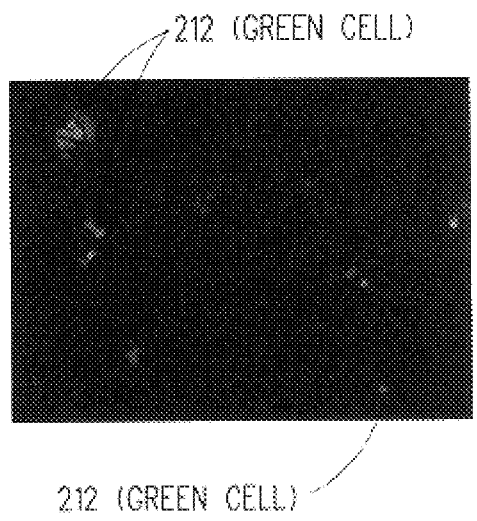

Referring to FIGS. 3C–3D, there are two photographs one of attached HEK 293 cells and another of transfected HEK 293 cells on the microplatforms 202 of the cell transfection microplatform apparatus 200. To demonstrate that surface-mediated transfection of cells can be performed on the top surface 206 of microplatforms 202, plasmid DNA (0.025 $\mu g/\mu l$)(foreign biomolecule 210) encoding for the Green Fluorescent Protein (GFP) dissolved in 0.20% gelatin was hand spotted by an inventor on the top surfaces 206 of oxygen plasma-treated silica microplatforms 202. The DNA spot covered all the microplatforms 202 in that given area. The microplatforms 202 containing the dried DNA spots were then incubated in an Effectine transfection reagent. The plate holding the microplatforms 202 was transferred to a cell culture dish with the microplatform 1202 side-up and then HEK 293 cells were added. Cells successfully attached to the top surfaces 206 of the microplatforms 202 and after 48 hours green transfected cells were observed on those microplatforms 202 to which DNA had been deposited. FIG. 3C shows a phase contrast image of the HEK 293 cells attached to the top surfaces 206 of the microplatforms 202. And, FIG. 3D shows the same field of microplatforms 202 using fluorescence microscopy, revealing those cells which were transfected and thus expressing the fluorescent GFP protein.

Figure 4:
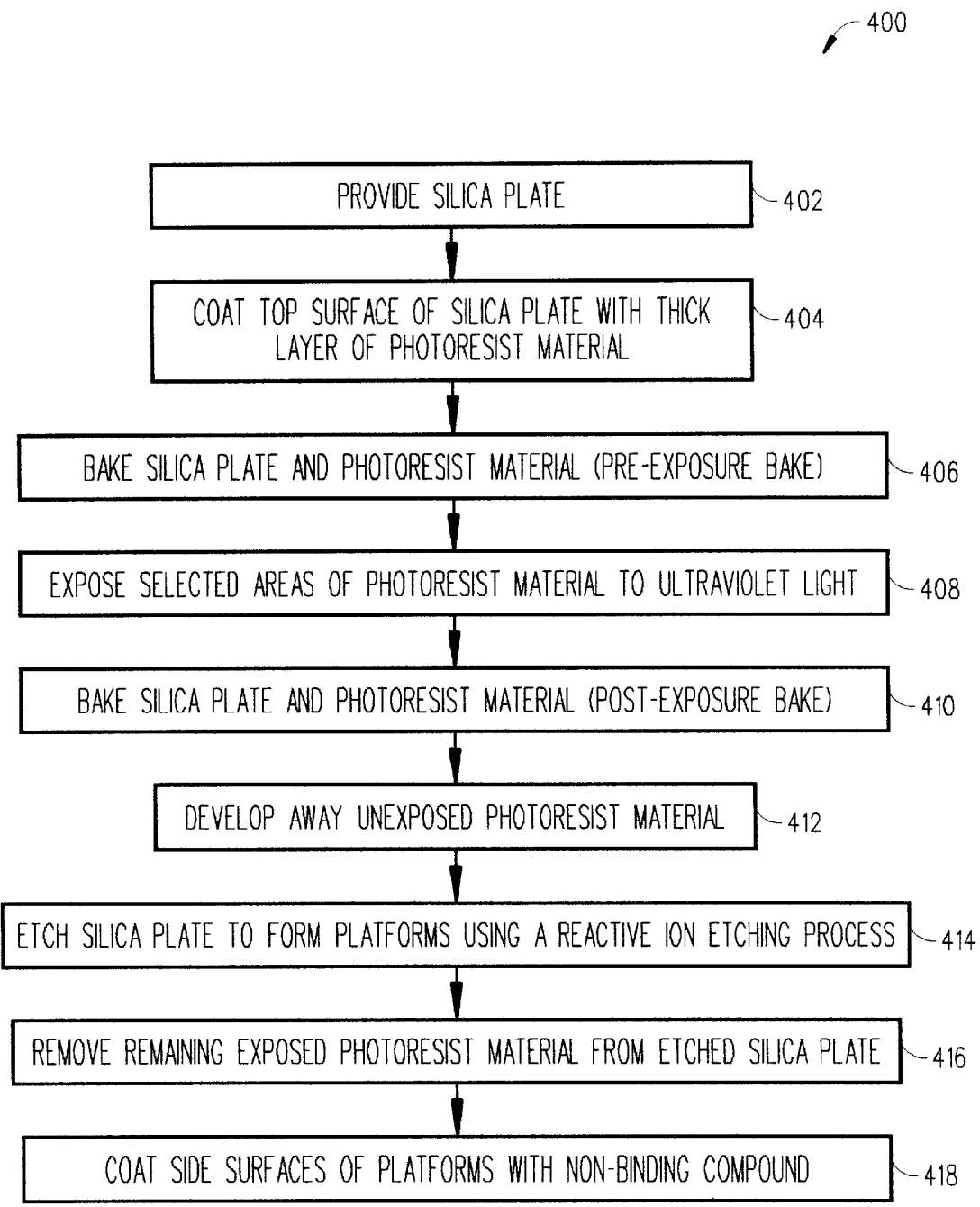
FIG. 4 is a flowchart illustrating the steps of a preferred method for making the first embodiment of the cell transfection apparatus shown in FIG. 2.

Referring to FIGS. 4 and 5, there are respectively illustrated a flowchart of a preferred method 400 for making the cell transfection microplatform apparatus 200 and various cross-sectional side views of the cell transfection microplatform apparatus 200 at different steps in the preferred method 300. To make the cell transfection microplatform apparatus 200, a silica plate 502 (e.g., silica wafer) is provided (step 402) and coated (step 404) with a substantially thick layer of photoresist material 504 (see FIG. 5A). To coat a top surface of the silica plate 502 with a desired thickness of photoresist material 504, the photoresist material 504 is spun onto the silica plate 502 at a speed based on the viscosity of the photoresist material 504.

The photoresist material 504 is preferably a negative-tone photoresist material with a thickness of approximately 200 μm. The negative-tone photoresist material 504 can be SU-8 photoresist material that is currently manufactured and sold by MicroChem Corporation. A detailed discussion about the physical and chemical characteristics of the SU-8 photoresist material 504 is provided in a concurrently filed U.S. patent application Ser. No. 09/962,831, by Michael B. Brady et al., which is incorporated herein by reference. It should be noted however that other types of materials besides the SU-8 photoresist material 504 and the silica plate 502 can be used to make the cell transfection microplatform apparatus 200.

The silica plate 502 and, in particular, the SU-8 photoresist material 504 is then baked (step 406) to remove solvent from the SU-8 photoresist material 504. For instance, the SU-8 photoresist material 504 and the silica plate 502 can undergo a pre-exposure bake at 95° C. for around four hours to remove the solvent from the SU-8 photoresist material. To keep internal stresses to a minimum, an initial bake at 65–70° C. for around 3 minutes can be performed prior to the pre-exposure bake.

Selected areas of the baked SU-8 photoresist material 504 that are not covered by a photomask 506 are then exposed (step 408) to ultraviolet light 508 (or similar light). Exposure to ultraviolet light 508 promotes cross-linking of the SU-8 photoresist material 504 not covered by the photomask 506 (see FIG. 5B). For instance, the ultraviolet light 308 exposure dose can be approximately 800 mJ/cm$^2$ for a SU-8 photoresist material 504 that is 200 μm thick. It should be understood that the shape of the microplatforms 202 which can be, for example, round, square with rounded corners, square . . . is defined by the shape of the image made by the photomask 506.

After exposure to the ultraviolet light 508, the silica plate 502 and the SU-8 photoresist material 504 are baked (step 410) to further polymerize the exposed SU-8 photoresist material 504. Typically, the SU-8 photoresist material 504 and the silica plate 502 undergo a post-exposure bake on a hot plate at a temperature between 95° C. and 200° C. for approximately 15 minutes.

Figure 5A:
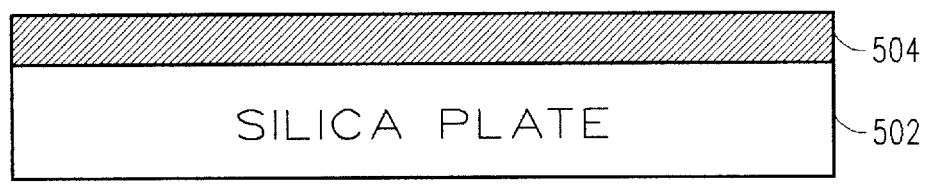
FIGS. 5A–5F are cross-sectional side views of the first embodiment of the cell transfection apparatus at different steps in the method shown in FIG. 4.
Figure 5B:
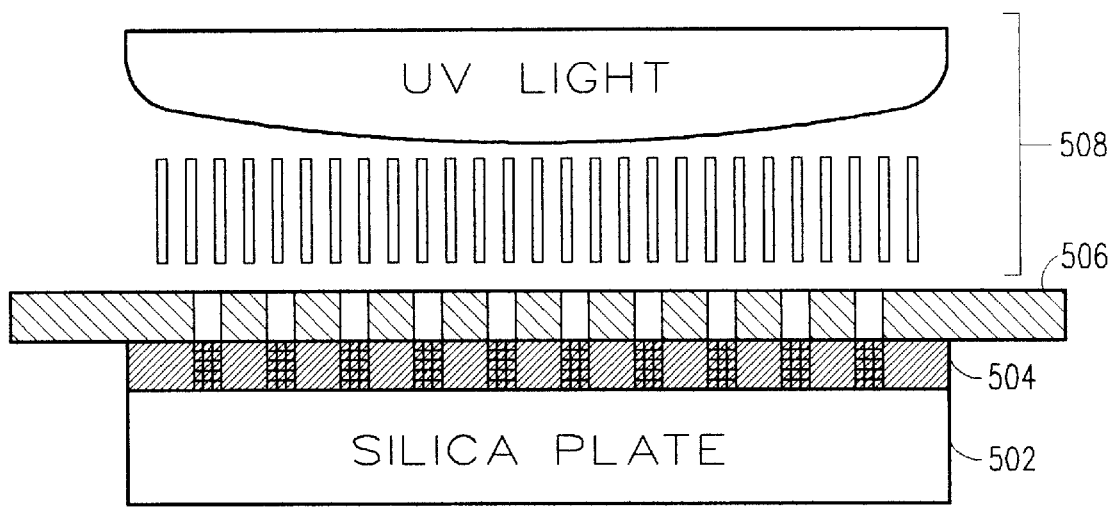
Figure 5C:
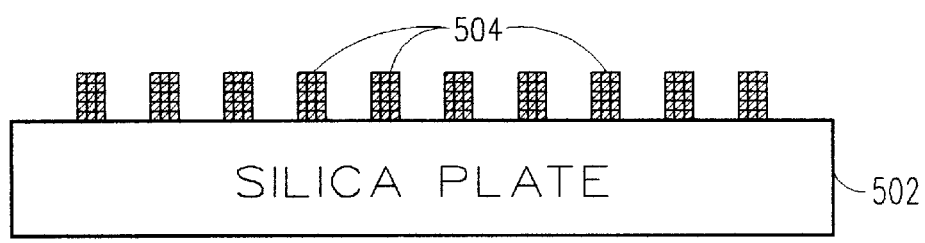
Figure 5D:
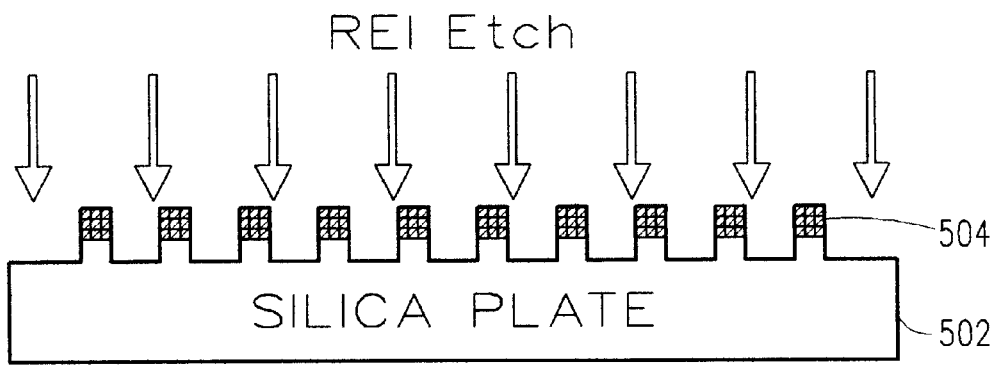
Figure 5E:
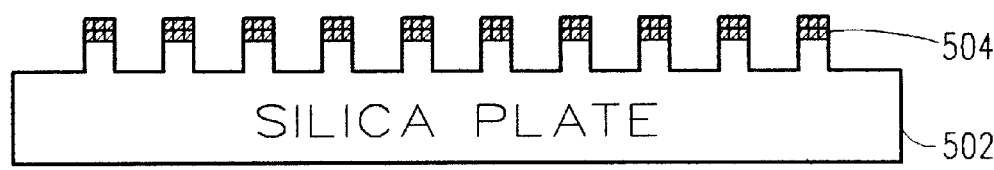

Upon completing the post-exposure bake, the unexposed SU-8 photoresist material 504 is developed (step 412) or removed from the silica plate 502 (see FIG. 5C). For instance, the unexposed SU-8 photoresist material 504 can be developed in a solvent such as PGMEA (propylene glycol methyl ether acetate). The unexposed SU-8 photoresist material 504 develop can be a three step process. First, an initial one-minute dip in PGMEA is performed. Second, a long dip is done in PGMEA for a time determined primarily by the thickness of the SU-8 photoresist material 504. Lastly as a rinse, a final dip in a fresh bath of PGMEA is used to rinse away any unexposed SU-8 photoresist material that remains on the silica plate 502.

At this point in the manufacturing process, the silica plate 502 and the polymerized SU-8 photoresist material 504 are subjected to a reactive ion etching (RIE) process (step 414). The RIE process effectively forms the microplatforms 202 in the silica plate 502 by etching away a predetermined amount of the top surface from the silica plate 502 that is not covered by the exposed SU-8 photoresist material 504 (see FIG. 5D). In particular, the RIE process can use a fluorocarbon etchant such as $CHF_3$ or $C_4F_8$. During the RIE process, it should be noted that a top layer of the exposed SU-8 photoresist material is also removed (see FIG. 5E). Moreover, it should be noted that the RIE process used in the present invention can be performed with or without using inductively coupled plasma.

Figure 5F:
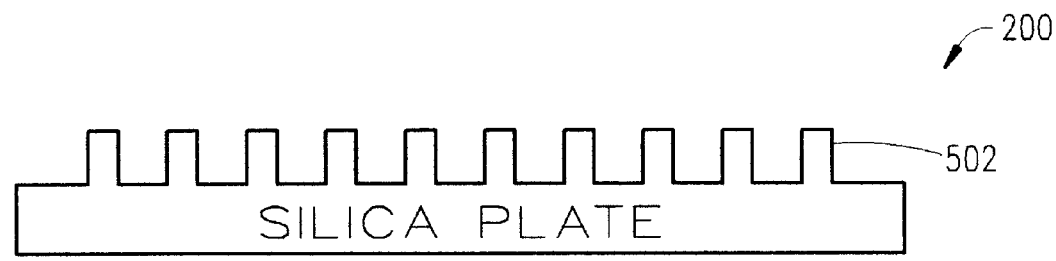

The remaining exposed SU-8 photoresist material 504 is then removed (step 416) from the silica plate 502 which now resembles the cell transfection microplatform apparatus 200 (see FIG. 5F). A variety of substance such as $CHF_3/O_2$, PG remover, piranha or nitric acid can be used to remove the remaining exposed SU-8 photoresist material 504. Thereafter, the side surfaces 208 of the microplatforms 202 and possibly the base 214 of the cell transfection microplatform apparatus 200 can be coated (step 418) with a non-binding compound including, for example, FDS or perfluorodecyltrichlorosilane.

It should be understood that the preferred method 300 is just one way to manufacture the cell transfection microplatform apparatus 200. Another way to manufacture the cell transfection microplatform apparatus 200 is to use an injection molding machine to mold a polymer into the cell transfection microplatform apparatus 200.

Figure 6A:
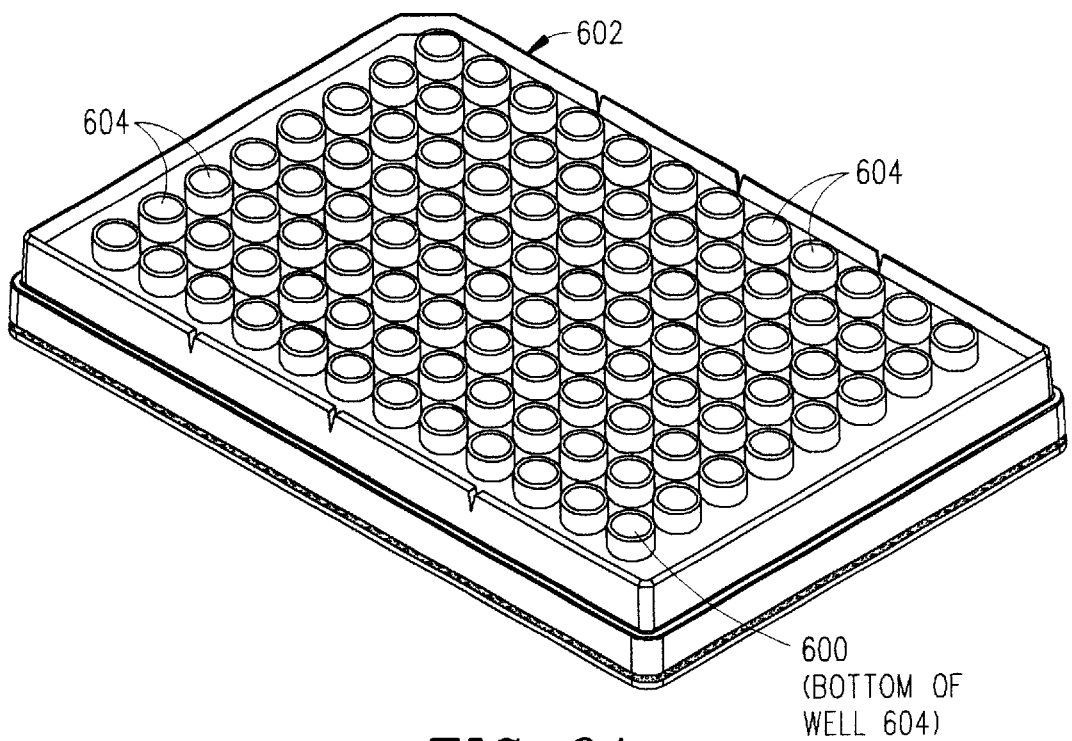
FIGS. 6A–6B illustrate a microplate (FIG. 6A) incorporating a second embodiment of a cell transfection apparatus (FIG. 6B) in accordance with the present invention.
Figure 6B:
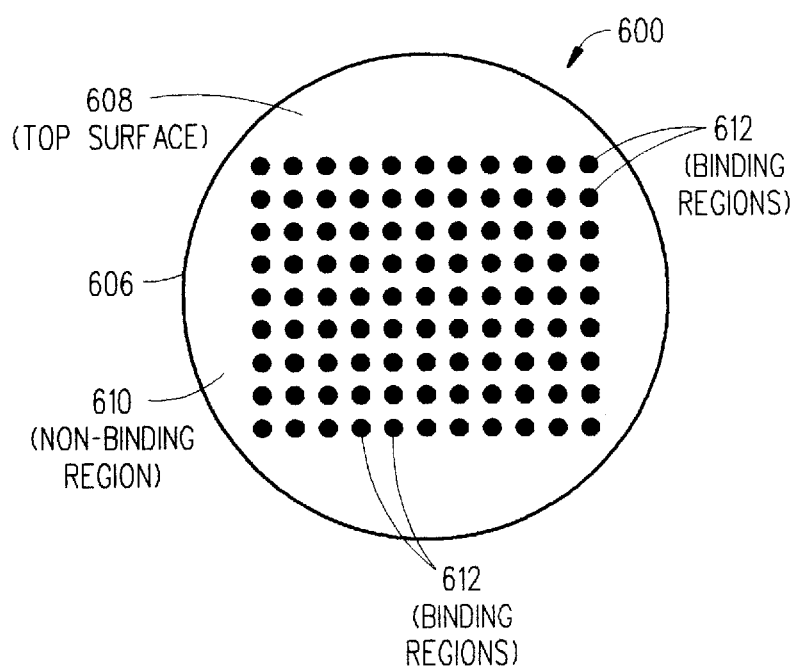

Referring to FIGS. 6A–6B, there are illustrated a perspective view of the cell transfection plate 600 (FIG. 6B) incorporated within a well 604 of a multiwell plate 602 (FIG. 6A). Although the cell transfection plate 600 is described as being incorporated within a well 604 of a multiwell plate 602 (e.g., microplate), it should be understood that the cell transfection plate 600 can be place within a wide-variety of devices such as a cell culture dish.

The cell transfection plate 600 includes a support structure 606 (e.g., silica plate) having a top surface 608 with a non-binding region 610 (only one shown) and one or more binding regions 612 (e.g., corrals). How the non-binding region 610 and the binding regions 612 (e.g., corrals) are formed is discussed below with respect to FIG. 9. Even though the binding regions 612 are shown in the shape of a circle, it should be understood that the binding regions 612 can have a wide-variety of shapes including, for example, squares, rectangles, triangles, ovals and polygons.

After creating the non-binding region 610 and the binding regions 612, one or more foreign biomolecules 210 (e.g., DNA, RNA, plasmids, oligonucleotides, nucleotides)(not shown) are printed onto each of the binding regions 612. In particular, all of the foreign biomolecules 210 can be printed at one time onto the binding regions 612. To accomplish this, a pin plate (not shown) is aligned over and then lowered into a series of capillaries (e.g., wells) in a redrawn reservoir (not shown) that contains the foreign biomolecules 210. After the pins on the pin plate have made contact with the foreign biomolecules 210, the pins are withdrawn and a portion of the foreign biomolecule(s) 210 in each of the wells remains on an end of each of the pins. Next, the pin plate is positioned over and then lowered down towards the cell transfection plate 600 until the foreign biomolecules 210 on the ends of the pins contacts the binding regions 612. After the foreign biomolecule(s) 210 on each pin has contacted the cell transfection plate 600, the pin plate is moved away from the cell transfection plate 600. As the pins are moved away from the cell transfection plate 600 at least a portion of the foreign biomolecules 210 remains on the binding regions 612. Other processes that can be used to print a high density array of foreign biomolecules 210 at the same time in the binding regions 612 include, for example, ink jet printing.

After printing the foreign biomolecules 210, a transfection reagent (e.g., Effectine, Lipofectamine, calcium phosphate, DEAE-dextran, cationic lipids) is added into the wells 604 of the microplate 602 and onto the printed foreign biomolecules 210. The lipid-based transfection reagent condenses and coats the printed foreign biomolecules 210 which are immobilized on the binding regions 612 with lipids. After a short incubation, the transfection reagent is removed. Alternatively, the transfection reagent can be mixed with the foreign biomolecules 210 and printed onto the binding regions 612 (e.g., corrals) of the cell transfection plate 600.

The desired cells 212 (e.g., HEK 293, COS-7, CHO) (see FIGS. 7–8) and cell growth media are poured into the wells 604 of the microplate 602 and onto the foreign biomolecules 210. The cells 212 (not necessarily all of the cells 212) settle and attach to the binding regions 612 (e.g., corrals). The cells 212 do not settle and attach to the non-binding region 610. As such, the cells 212 attached to the binding regions 612 become transfected with one or more foreign biomolecules 210 while the cells 212 located over the non-binding region 610 fail to become transfected with one or more foreign biomolecules 210. This type of transfection process is known as a reverse transfection process. It should be understood that the transfection reagent can be added to the mixture of cells 212 and cell growth media before they are poured into the wells 604 of the multiwell plate 602. Instead of adding the transfectant reagents and the cells at different times like described above.

To generate the transfection cell array, the cells 212 attached to each binding region 612 (e.g., corral) become transfected by the printed foreign biomolecule(s) 210 and as such express the protein(s) encoded by the printed foreign biomolecule(s) 210. In other words, each binding region 612 (e.g., corral) supports the growth of a group of transfected cells 212 that express one or more proteins. As such, the cell transfection plate 600 can be used to generate an array of transfected cells 212 which express as many different proteins as there are different printed foreign biomolecules 210. To confirm the expression of each foreign biomolecule 210 within each cell cluster, a DNA plasmid construct may be used that produces a fusion protein between the protein of interest and a Green Fluorescent Protein (GFP).

It should also be understood that the cell transfection microplatform apparatus 200 can also be incorporated within or formed within a bottom of a microplate 602.

Figure 7A:
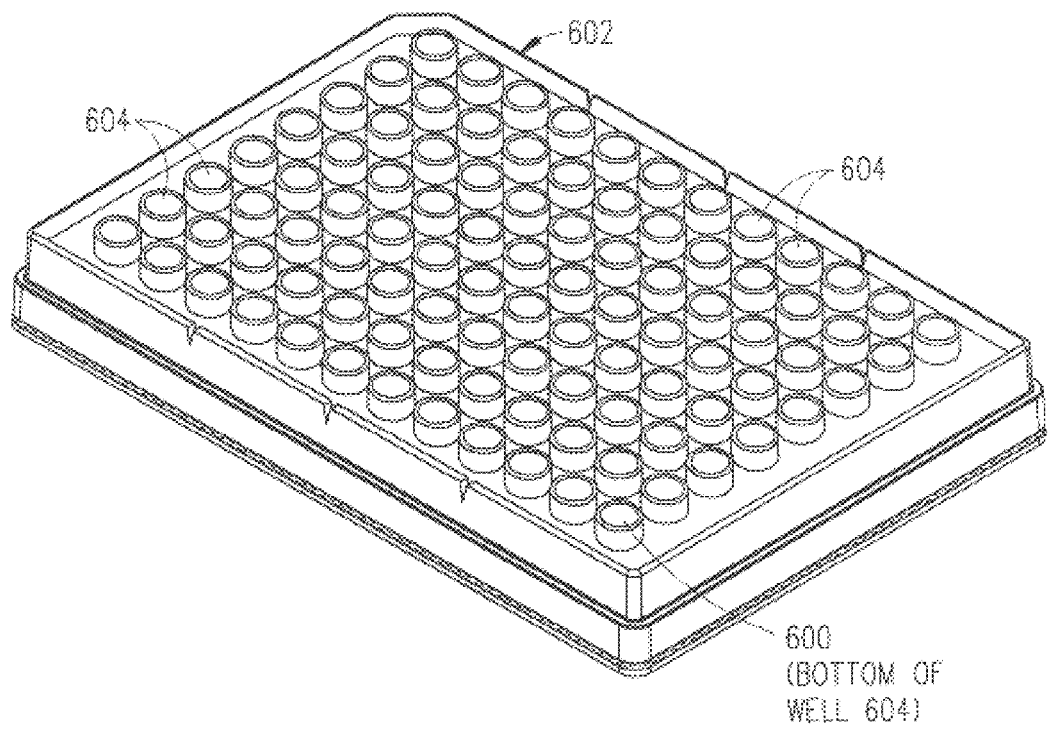
FIGS. 7A–7D illustrate microplates (FIGS. 7A and 7C) in which various cells (FIGS. 7B and 7D) were grown using the second embodiment of the cell transfection apparatus shown in FIG. 6B.
Figure 7B:
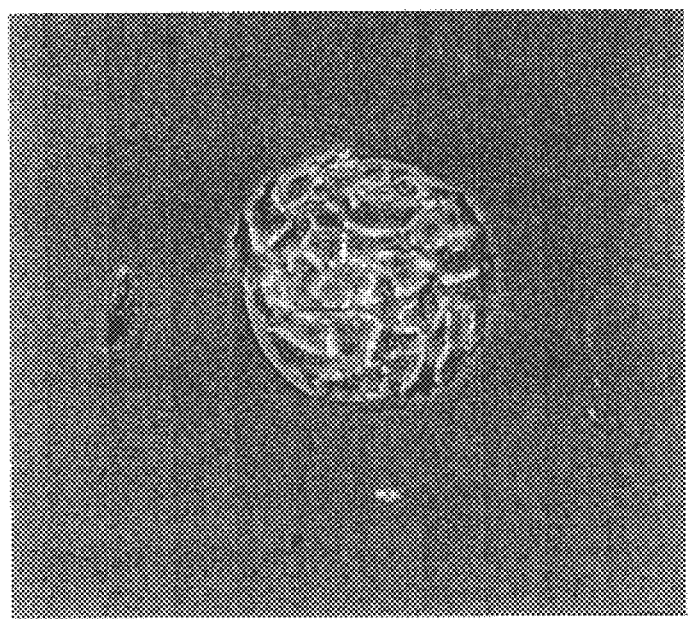
Figure 7C:
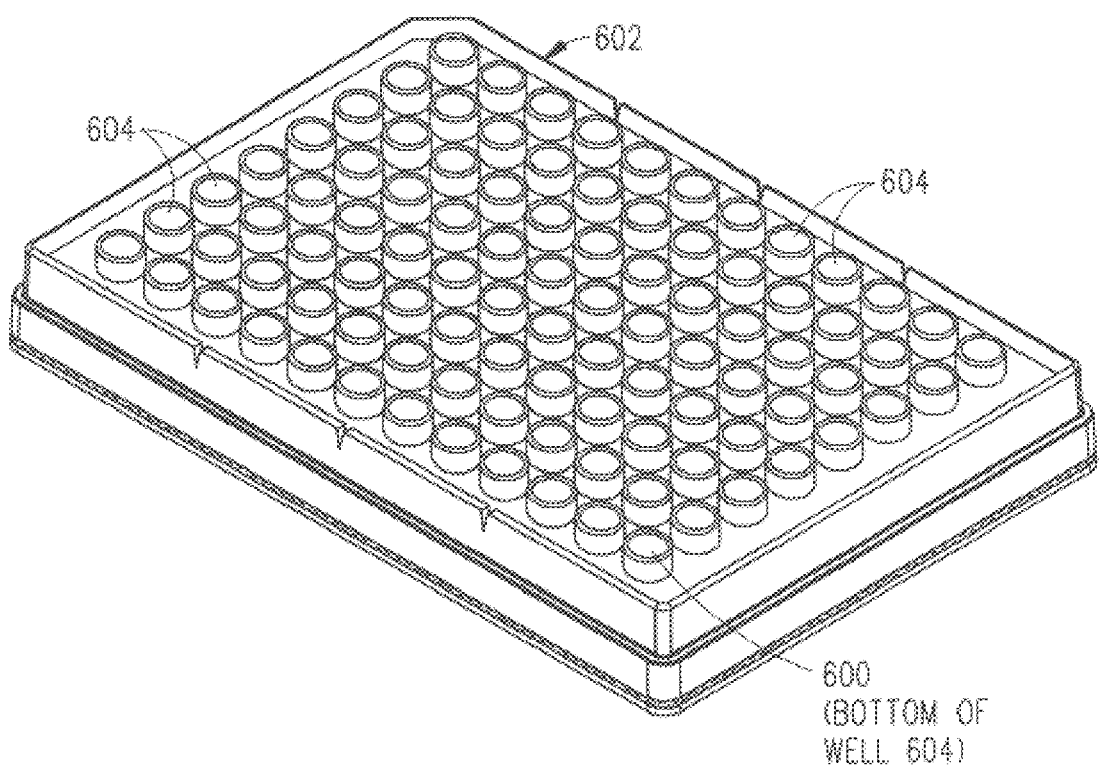
Figure 7D:
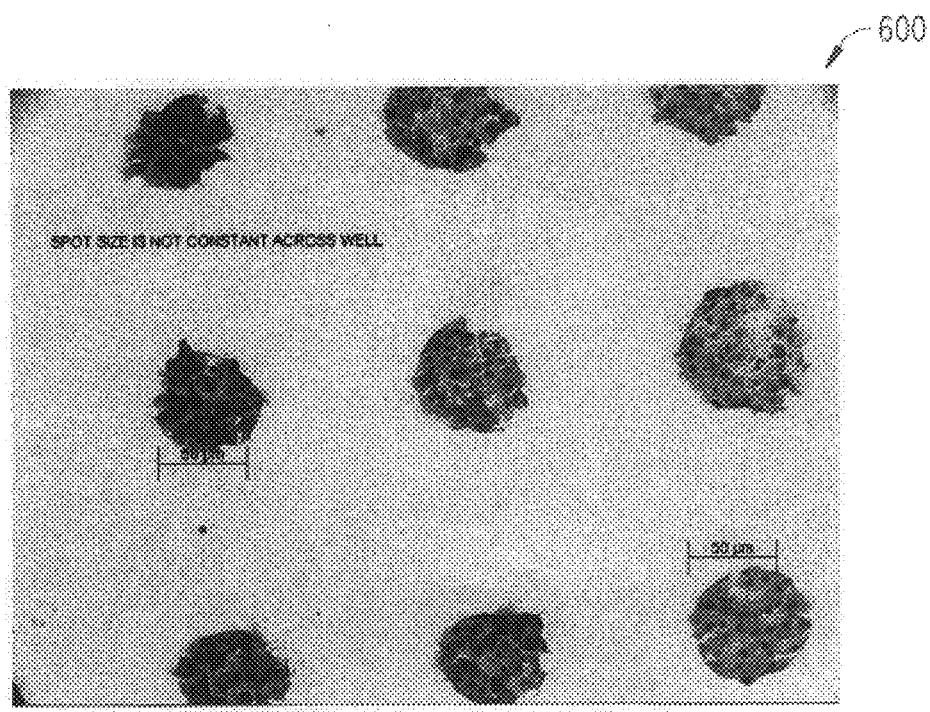

Referring to FIGS. 7A–7D illustrate microplates 602 (FIGS. 7A and 7C) incorporating one or more cell transfection plates 600 on which there was grown cells 212 (FIGS. 7B and 7D). The cell transfection plates 600 are located in the bottom of a 96 polystyrene 96 well plate 602. In these examples, normal rat kidney cell(s) 212 are respectively shown in binding regions 612 (e.g., corrals) that are 200 $\mu$m (see photograph in FIG. 7B) and 50 $\mu$m (see photograph in FIG. 7D) in diameter.

Figure 8:
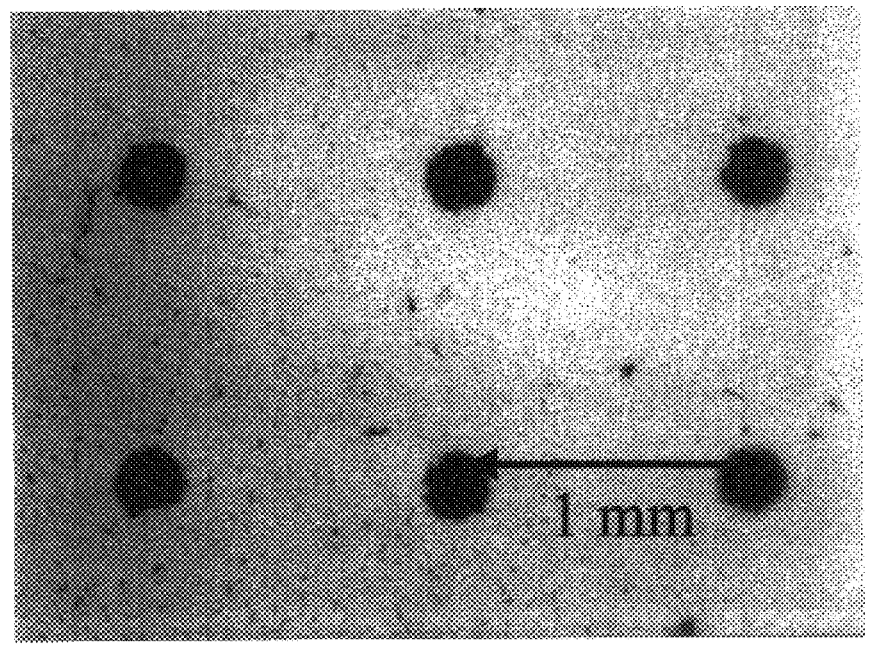
FIG. 8 is a photograph of various cells grown using the second embodiment of the cell transfection apparatus shown in FIG. 6.

Referring to FIG. 8, there is illustrated a photograph of NRK cells 212 attached to the binding regions 612 (e.g., corrals) of the cell transfection plate 600. These NRK cells 212 have been stained with a violet stain. In this example, the cell transfection plate 600 is a soda lime glass plate (borosilicate glass can also be used) that was placed in a dish (not shown) to grow NRK cells 212.

Figure 9:
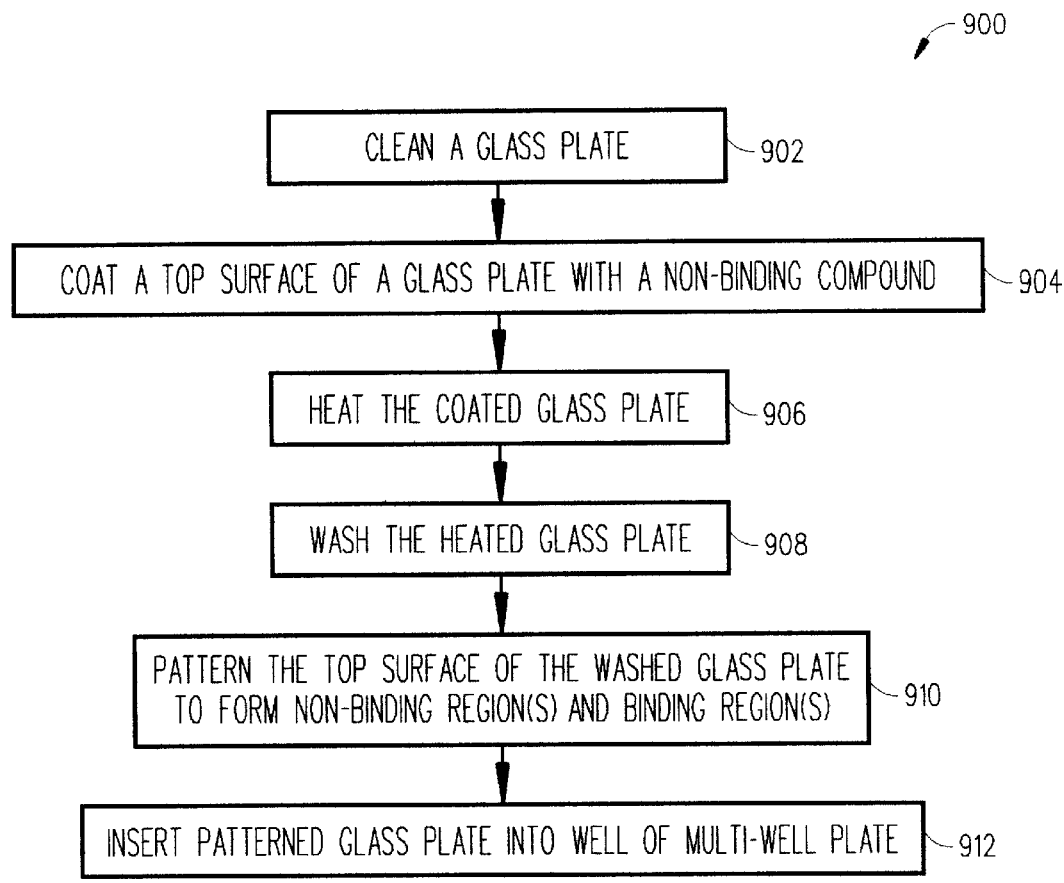
FIG. 9 is a flowchart illustrating the steps of a preferred method for making the second embodiment of the cell transfection apparatus shown in FIG. 6.

Referring to FIG. 9, there is a flowchart illustrating the steps of a preferred method 900 for making the cell transfection plate 600. To make the cell transfection plate 600, a glass plate (e.g., support structure 606) is cleaned (step 902). In the preferred embodiment, the glass plate (e.g., support structure 606) which is approximately 110 mm×75 mm×0.22 mm thick can be cleaned as follows: (1) soaked in a bath containing 0.1% Contrad 70 detergent in MilliQ water; (2) rinsed with MilliQ water; (3) dipped into HPLC grade acetone; (4) dipped into HPLC grade hexane; (5) dried in a heated oven at 130° C.; and (6) exposed to an oxygen or argon plasma for 10 minutes. Thereafter, the cleaned glass plate (e.g., support structure 606) is often visually inspected to make sure it is clean.

The cleaned glass plate (e.g., support structure 606) is coated (step 904) with a non-binding compound. To coat the cleaned glass plate (e.g., support structure 606), the cleaned glass plate can be dipped in a non-binding solution and transferred to a glass rack. In the preferred embodiment, the non-binding compound is PEOSi (Silquest A-1230 polyalkyleneoxidealkoxysilane) which is mixed with glacial acetic acid (990 $\mu$L of PEOSi and 10 $\mu$L of acetic acid) and diluted 1:99 by volume with absolute ethanol. The ethanol is a solvent for the PEOSi which is used because the PEOSi is viscous by itself and would not form an even coating on the glass plate. The final non-binding solution contains ~99% ethanol and ~1% acidified PEOSi solution. The non-binding solution is then filtered through a disposable syringe 0.45 $\mu$m PTFE filter to remove any particulate matter. Preferably, the PEOSi forms a monolayer coating that is approximately 15 Å thick.

A detailed discussion about the physical and chemical characteristics of PEOSi (Silquest A-1230 polyalkyleneoxidealkoxysilane) is provided below. Basically, PEOSi includes nonionic hydrophilic molecules that have repeat units of polyethylene oxide with a terminal alkoxysilane. The alkoxy group(s) on the silane is cleaved by acetic acid resulting in a reactive Si group that can react with the SiOH on the surface of the glass plate. Therefore, the PEOSi-group bonds to the glass plate. The PEO functionality is non-ionic hydrophilic and acts as a layer of water on the surface of the glass plate thus inhibiting the attachment of cells and proteins to the top surface of the glass plate.

The Silquest A-1230 has the following molecular structure and properties:

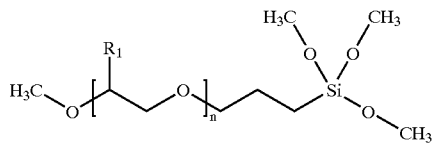

In particular, the Silquest® A-1230 silane, gamma-(Polyalkylene oxide)propyltrimethoxysilane, has the following physical properties:

| | |
|---|---|
| Physical Form | amber liquid |
| Molecular Weight | proprietary |
| Specific Gravity (25/25) | 1,076 |
| Boiling Point | >150° C. (302° F.) |
| Freezing Point | −8° C. (18° F.) |
| Flash Point* | 87° C. (189° F.) |

*Determined by ASTM Method D 93 using the Pensky-Martens closed cup.

It should be noted that a variety of non-binding compounds now known or subsequently developed that have similar properties to Silquest® A-1230 can be used in the present invention. For example, a non-binding compound that is used in the present invention should have the following qualities: (1) the non-binding compound should not redissolve in water; and (2) the non-binding compound should stick to glass. One such molecule similar to Silquest A-1230 is sold by Gelest, Inc. it is 2-[methoxy(polyethyleneoxy)propyl]trimethoxysilane with a formula of $CH_3(OC_2H_4)$ $6-9(CH_2)_3OSi(OCH_3)_3$ and a molecular weight=460–590 D.

Referring back to the flowchart of the preferred method 900, the coated glass plate (e.g., support structure 606) is dried (step 906). In the preferred embodiment, the coated glass plate is placed in a 130° C. oven for 20 minutes to dry the non-binding solution.

Next, the dried glass plate (e.g., support structure 606) is washed (step 908). In the preferred embodiment, the dried glass plate is washed with MilliQ water to remove any excess non-binding solution and then the glass plate is either air dried or dried in nitrogen.

Thereafter, the washed glass plate (e.g., support structure 606) is patterned (step 910) so as to remove pre-selected portions of the non-binding compound from the top surface in order to form the binding regions 612 (e.g., corrals). In the preferred embodiment, a laser (e.g., excimer laser, carbon dioxide laser) is used to pattern the washed glass plate (e.g., support structure 606) by removing selected portions of the non-binding compound and thus exposing the binding regions 612 located in the areas under the removed non-binding compound. At this point, the patterned glass plate resembles the cell transfection plate 600 (see FIG. 6).

In experiments conducted by one of the inventors, the results of which are shown in Table 1, a washed glass plate (e.g., support structure 606) was patterned using an excimer laser and a mask. Basically, the result was that the inventor was able to generate excellent patterns with a mask where 0.1-mm diameter spots were separated 1-mm center to center. Good binding regions 612 (e.g., corrals) were made using the following laser settings: (1) laser power, ~0.27 $J/cm^2$; (2) frequency, range of 20 to 100 Hz/sec.; and (3) total number of pulses, range of 250 to 1000. However, at a very high laser power and/or a high pulse rate the glass plate (e.g., support structure 606) cracked from the heat that was generated.

TABLE 1

| Experiment # | Name = Hz per sec/ pulses | Wavelength, nm | Mask/ No Mask | Substrate | Coating | Power, J/cm2 | Frequency, Hz/sec | Pulses | Comments Cell corral images |
|---|---|---|---|---|---|---|---|---|---|
| 1 | 100/5 | 248 | Mask | glass | SiN BS | 0.27 | 100 | 5 | |
| 1 | 100/100 | 248 | Mask | glass | SiN BS | 0.27 | 100 | 100 | |
| 1 | 100/500 | 248 | Mask | glass | SiN BS | 0.27 | 100 | 500 | |
| 3 | 200/100 | 248 | Mask | glass | SiN BS | 0.27 | 200 | 100 | |
| 3 | 200/250 | 248 | Mask | glass | SiN BS | 0.27 | 200 | 250 | messy |
| 3 | 200/500 | 248 | Mask | glass | SiN BS | 0.27 | 200 | 500 | very good clear pattern |
| 3 | 200/1000 | 248 | Mask | glass | SiN BS | 0.27 | 200 | 1000 | very good clear pattern |
| 3 | 100/100 | 248 | Mask | glass | SiN BS | 0.27 | 100 | 100 | good |
| 3 | 100/250 | 248 | Mask | glass | SiN BS | 0.27 | 100 | 250 | very good clear pattern |
| 3 | 100/500 | 248 | Mask | glass | SiN BS | 0.27 | 100 | 500 | very good clear pattern |
| 3 | 100/1000 | 248 | Mask | glass | SiN BS | 0.27 | 100 | 1000 | very good clear pattern |
| 3 | 20/100 | 248 | Mask | glass | SiN BS | 0.27 | 20 | 100 | good |

TABLE 1-continued

| Experiment # | Name = Hz per sec/ pulses | Wavelength, nm | Mask/ No Mask | Substrate | Coating | Power, J/cm2 | Frequency, Hz/sec | Pulses | Comments Cell corral images |
|---|---|---|---|---|---|---|---|---|---|
| 3 | 20/250 | 248 | Mask | glass | SiN BS | 0.27 | 20 | 250 | sloppy |
| 3 | 20/500 | 248 | Mask | glass | SiN BS | 0.27 | 20 | 500 | sloppy |
| 3 | 20/1000 | 248 | Mask | glass | SiN BS | 0.27 | 20 | 1000 | very good clear pattern |
| 4 | 20/100 | 248 | No Mask | glass | SiN BS | 0.27 | 20 | 100 | |
| 4 | 20/250 | 248 | No Mask | glass | SiN BS | 0.27 | 20 | 250 | |
| 4 | 20/500 | 248 | No Mask | glass | SiN BS | 0.27 | 20 | 500 | |
| 4 | 20/1000 | 248 | No Mask | glass | SiN BS | 0.27 | 20 | 1000 | |
| 13 | 10/10 | 248 | Mask | glass | SiN BS | 0.37 | 10 | 10 | |
| 13 | 10/100 | 248 | Mask | glass | SiN BS | 0.37 | 10 | 100 | |

*Control Glass coated with NBS.

Referring back to the flowchart of the preferred method 900, the patterned glass plate (e.g., support structure 606) can be inserted (step 912) into a well 604 of a multiwell plate 602 (see FIG. 6). It should be noted that the foreign biomolecules 210 can be printed either before of after the cell transfection plate 600 is inserted into the multiwell plate 602 (e.g., microplate). Moreover, it should be understood that the patterned glass plate can have 96 distinct support structures 606 (for example) formed thereon which is adhered. (e.g., glued) to the bottom of a 96 well microplate 602.

Figure 10:
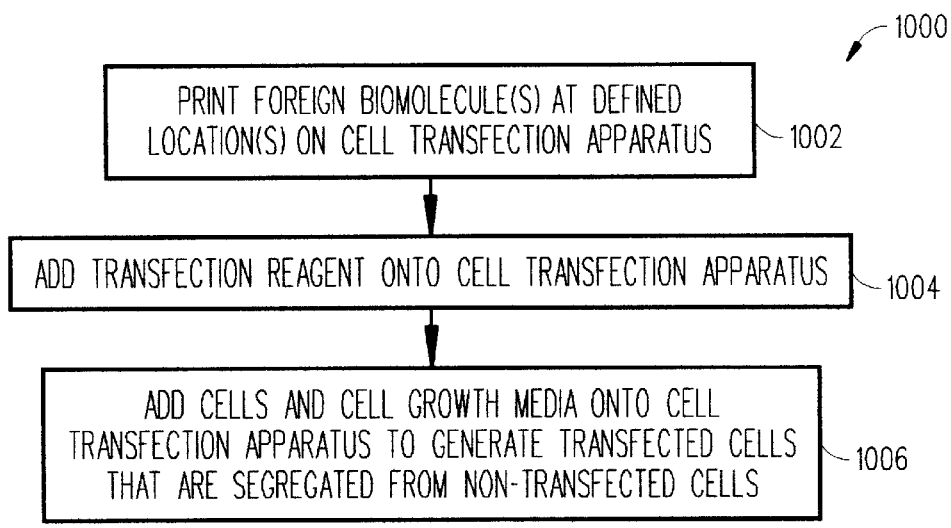
FIG. 10 is a flowchart illustrating the steps of a preferred method for using the cell transfection apparatuses shown in FIGS. 2 and 6.

Referring to FIG. 10, there is a flowchart illustrating the steps of a preferred method 1000 for using the cell transfection apparatus (e.g., cell transfection microplatform apparatus 200, cell transfection plate 600). First, the foreign biomolecule(s) 210 are printed (step 1002) at defined locations on a surface of the cell transfection apparatus. In the first embodiment, the foreign biomolecules 212 are printed on the top surfaces 206 of the microplatforms 202 extending from the cell transfection microplatform apparatus 200 (see FIG. 2). In the second embodiment, the foreign biomolecules 212 are printed on the binding regions 612 (e.g., corrals) of the cell transfection plate 600 (see FIG. 6). It should be noted that different foreign biomolecules 210 can be printed or positioned onto one or more binding regions 612 (e.g., corrals) of the cell transfection plate 600. As such, each binding region 612 might have a unique sequence or each binding region 612 might have some redundancies of sequences. The same is true for the cell transfection microplatform apparatus 200.

It should be understood that the foreign biomolecules 210 (e.g., DNAs, RNAs, plasmids, oligonucleotides, nucleotides) could be contained in a solvent or ink containing materials such as agar, collagen, gelatin, alginate gel, starch derivative, dextran, or other protein material that is not cytotoxic for eucaryatic cells 212.

The transfection reagent is added (step 1004) onto the surface of the cell transfection apparatus. In the first embodiment, the transfection reagent is added to the top surfaces 206 of the microplatforms 202 extending from the cell transfection microplatform apparatus 200 (see FIG. 2). In the second embodiment, the transfection reagent is added to the binding regions 612 (e.g., corrals) of the cell transfection plate 600 (see FIG. 6). Again, the transfection reagent is incubated for a period of time and then removed from the cell transfection apparatus. Other ways of adding and removing the transfection reagent to and from the cell transfection apparatus have been described above. For example, the transfectant reagent can be added by itself, mixed with the foreign biomolecules 210, or mixed with the cell growth media.

Next, the cells 212 and the cell growth media are added (step 1006) onto the surface of the cell transfection apparatus. In the first embodiment, the cells 212 and cell growth media are added until they cover the top surfaces 206 of the microplatforms 202 extending from the cell transfection microplatform apparatus 200 (see FIG. 2). In the second embodiment, the cells 212 and cell growth media are added until they cover to the non-binding regions 610 and the binding regions 612 (e.g., corrals) of the. cell transfection plate 600 (see FIG. 6).

In accordance with the transfection process, the transfection reagent functions as a carrier to enable the foreign biomolecule 210 to enter into the eucaryatics cells 212 that have attached to the microplatforms 202 of the cell transfection microplatform apparatus 200 and attached to the binding regions 612 (e.g., corrals) of the cell transfection plate 600. The uptake of transfection complex by the cell 212 can take place within a period of 0.5 to 6 hours. Common commercial transfection reagents include (for example): (1) DOTAP™, a moncationic compound liposome formulation; (2) DOSPER™, a liposomal formulation of a polycationic compound; (3) Fugene 6™, a non-liposomal blend of lipids and other compounds; (4) X-tremeGENE Q2 Transfection Reagent for HeLa, Jurkat and K-562 cell types; (5) SuperFect™, an actvated dendrimer (6) Efectene a cationic non-liposomal lipids formulation; and 97) CLONfectin™ a cationic, amphiphilic lipid.

There are many different types of adherent eucaryatics cells can be used to grow the transfection cell arrays. A list of some of the cell lines that could be used are: 10.1 mouse fibroblasts, 13-5-1 Chinese hamster ovary epithelial, 132-d5 human fetal fibroblasts; HEK-293 human epithelial kidney; 3T3 or 3T3 NIH or 3T3 Swiss or 3T3 -L1 mouse embryo fibroblast; BALB/3T3 mouse embryo fibroblast; BHK-21 baby hamster kidney fibroblasts; BS-C-1 monkey kidney epithelial; C2 rat liver epithelial, C2C12 mouse muscle fibroblast, C2H mouse embryo fibroblast; C4, C6 Caco-2 human adenocarcinoma epithelial cells, CHO or CHO-7 or CHO-IR or CHO-K1 or CHO-K2 or CHO-T or CHO Dhfr −/−Chinese hamster ovary epithelial; COS or COS-1 or COS-6 or COS-7 or COS-M6A African green monkey kidney, SV40 transformed fibroblast; HeLa or HeLa B or HeLa T4 human cervix carcinoma epithelial; Hep G2 human hepatoblastoma epithelial; MDCK (NBL-2) canine kidney epithelial; MEF mouse embryo fibroblast; MRC-5; NRK or NRK-52E normal rat epithelial etc.

The efficiency of the transfection can be monitored using direct or indirect assay methods. For example, the cells 212 can incorporate a reporter gene which is used to confirm the protein expression of the foreign biomolecules 210. Common reporter genes include, for example, green fluorescent protein (GFP), chloramphenical acetyl transferase for a CAT ELISA immunological assay, firefly luciferase, β-galactosidase, or human growth hormone (hGH).

The transfected cells 212 can express different types of proteins that are useful for drug testing such as: (1) liver enzymes for an ADME and toxicology assay; (2) cytokine, growth factor and hormone receptors e.g. epidermal growth factor receptor (EGF-R), fibroblast growth factor receptor 1 (FGFR-1, FGFR-2, FGFR-3); insulin-like growth factor binding proteins (protein-1, (IGFBP-1/GF-1 complex) protein-1/GF-1 complex, (IGFBP-2) protein-2, IGFB-3, insulin receptor (a receptor protein tyrosine kinase that mediates the activity of insulin,; Interleukin receptors (IL-1, sRI, IL-1RacP, IL-2 sRα, IL-2 sRβ, IL-18); leptin receptors; VEGF receptors (R1, flk-1, Flt-4, tie-1, tek/tie-2); androgen receptor, estrogen receptors (ER, ER-β,), (3) adrenergic neurotransmitter receptors, (4) other neurotransmitters ($Cb_2$, $D_1$, $D_{2long}$, D3, D2,4, M1, M2, M3, serotonin receptors (5-$HT_{1A}$, 5-$HT_6$ 5-$HT_7$), nicotinic acetylcholine receptors, muscarinic acetylcholine receptors, (5) calcium channels, (6) angiogenesis regulators, and (7) G proteins and g-protein coupled receptors. Once the transfected cells 212 have expressed the proteins of interest, one or more drug candidates can be added to the cell transfection apparatus. Small quantities of drug candidates can be used and tested against many virtual cell types.

Following are some advantages, features and uses of the present invention:

In the cell transfection microplatform apparatus 200, the transfected cells 212 are located on the microplatforms 202 and the non-transfected cells 212 are located on the top surface 205 of the support structure 204 such that the transfected cells 212 are segregated from the non-transfected cells 212 (see FIG. 2).

In the cell transfection plate 200, the transfected cells 212 are located on the binding regions 612 (e.g., corrals) and the non-transfected cells 212 are located over the non-binding regions 610 such that the transfected cells 212 are segregated from the non-transfected cells 212 (see FIG. 6).

The cell transfection apparatus allows for easier registry because the position of each group of transfected cells 212 can be easy to locate based on the positions of the microplatforms 202 (see FIG. 2) and the non-binding regions 612 (see FIG. 6).

The cell transfection apparatus allows for easier imaging because the transfected cells 212 are located at known positions on the microplatforms 202 (see FIG. 2) and the non-binding regions 612 (see FIG. 6).

The cell transfection microplatform apparatus 200 can further reduce cross-contamination between DNA spots. Since the DNA is printed on elevated microplatforms 202 there is created the opportunity for loosely bound DNA once free to settle down on the top surface 205 of the support structure 204, lowering the probability that the loose DNA will contaminate neighboring spots.

The cell transfection apparatus can be used in a high throughput fashion to study potentially thousands of different proteins within a single experiment. Such an array could be used for:

Receptor Array: print the genes for a class of receptor on an array. Use this array to screen for binding of novel ligands with unknown receptor pairings.

Functional Theme Array: to be used in drug screening with the following applications as examples:

Signal transduction pathway array: print the genes for all the components of a signal transduction pathway and screen for compounds that block the pathway at a desired step.

Kinase array: print the genes of all known kinases. This could be used to screen compound libraries for inhibitors of kinases.

Oncogene array: print genes of all known oncogenes. This could be used to screen compound libraries for inhibitors of oncogenes (e.g., anti-cancer drugs). This could also be used to print unkown genes and screen for genes that promote cell proliferation (e.g., putative oncogenes).

Array of genes of unknown function: printing thousands of genes of unknown function. This could be used to screen for ligands for orphan receptors. This could also be used to screen for any desired biological phenotype.

The cell transfection plate 600 incorporated within a multiwell plate enables the researcher to view each corral within the transfection array the size of which can correspond to the spatial resolution of the optical imaging instrument that is used to analyze the data. A usual geometry is 50 to 400 micron spots separated by at least the diameter of the patterned spots. The multiwell plates can have 96, 384 or even 1536 wells.

The cell transfection apparatus can be used in the drug discovery process in applications including, for example, SAR (structure activity relationships), ADME (adsorption, distribution, metabolism, and excretion studies), toxicity studies, diagnostics, and high throughput screening. These cell arrays can be used with high content images that can collect data from the transfected cells. The assay can utilize fluorescent labels, radiolabels, chemiluminescent methods, or optical imaging of the cells within the corral to identify morphological changes. The optics include confocal, polarization, epifluorescence and simples microscopy. These methods would be used to image either the inside of the cells, the exterior surface, the general shape, the viability of the cells, the growth rate of the cells, the cell cycle stage, and the extend of differentiation of the cells.

Another advantage of such arrays of unique cells in each well of a microwell plate is that many responses can be measured using a small quantity of a drug candidate in each well. This conserves drug libraries. There can be multiple responses within the well e.g. the drug compound could be an agonist to proteins found in cells in one corral and an antagonist to proteins in cells in another corral. The drug candidate could kill the cells in most of the corrals and leave viable cell populations in other corrals.

Yet another advantage of cells cultured in microwell plates is that they can easily be maintained in standard incubators. The cells and the media can be easily and accurately dispensed using existing dispensing robotics. There is a sufficient volume of medium within each well to provide the needed nutrients to maintain many common lines of adherent cell lines. In contrasts, micro-cell arrays and cassettes would require microfluidics to dispense the drug candidates and to maintain fresh medium within the wells.

Although only two embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A cell transfection plate, comprising:
   a support structure having a top surface with at least one binding region and at least one non-binding region, wherein said at least one non-binding region separates transfected cells adhered to one binding region from other transfected cells adhered to other binding regions.

2. The cell transfection plate of claim 1, wherein said transfected cells located in each binding region have undergone a transfection process in which cells become transfected cells by attaching at least one foreign biomolecule, including nucleic acids, to the at least one binding region and adding a transfectant reagent and cells in a cell growth media onto the top surface such that at least a portion of the cells adhered to the at least one binding region expresses at least one protein encoded by the at least one foreign biomolecule and becomes said transfected cells.

3. The cell transfection plate of claim 2, wherein each foreign biomolecule is attached at one time onto the at least one binding region.

4. The cell transfection plate of claim 2, wherein said at least one foreign biomolecule includes a DNA, RNA, or oligonucleotide.

5. The cell transfection plate of claim 2, wherein said transfection reagent is added, incubated and then removed before adding the cells and the cell growth media onto said top surface.

6. The cell transfection plate of claim 2, wherein said transfection reagent is mixed with said at least one foreign biomolecule.

7. The cell transfection plate of claim 2, wherein said transfection reagent is mixed with said cells and said cell growth media.

8. The cell transfection plate of claim 2, wherein said at least one non-binding region is coated with a non-binding compound.

9. The cell transfection plate of claim 8, wherein said non-binding compound includes nonionic hydrophilic molecules that have repeat units of polyethylene oxide with a terminal alkoxysilane.

10. The cell transfection plate of claim 2, wherein said transfected cells incorporate reporter genes used to confirm an expression of the at least one foreign biomolecule.

11. The cell transfection plate of claim 2, wherein said support structure is incorporated within a well of a multiwell plate.

12. A method for making a cell transfection plate, said method comprising the steps of:
    coating a top surface of a support structure with a non-binding compound;
    heating the coated support structure;
    washing the coated support structure; and
    patterning the top surface of the washed support structure so as to remove portions of the non-binding compound to form at least one binding region, wherein the patterned support structure resembles the cell transfection plate.

13. The method of claim 12, further comprising the step of inserting the patterned support structure into a well of a multiwell plate.

14. The method of claim 12, wherein said step of patterning further includes a step of using a laser to remove portions of the non-binding compound to form the at least one binding region.

15. The method of claim 12, wherein said non-binding compound includes nonionic hydrophilic molecules that have repeat units of polyethylene oxide with a terminal alkoxysilane.

16. A method for injecting a cell with a foreign biomolecule, said method comprising the steps of:
    attaching, to defined locations in at least one binding region on a support structure, at least on foreign biomolecule, including nucleic acids;
    adding, onto the support structure, a transfection reagent; and
    adding, onto the support structure, cells and cell growth media, wherein said support structure is configured such that the cells that become transfected cells in one binding region are separated by at least one non-binding region on the support structure from other transfected cells located in other binding regions.

17. The method of claim 16, wherein said step of attaching at least one foreign biomolecule includes the step of attaching at one time all of the foreign biomolecules.

18. The method of claim 16, wherein said added transfection reagent is incubated and then removed before adding the cells and the cell growth media onto said support structure.

19. The method of claim 16, wherein said at least one foreign biomolecule includes a DNA, RNA, or oligonucleotide.

20. The method of claim 16, wherein said support structure is used for high-throughput screening in a drug discovery process.

21. A cell transfection microplatform, comprising:
    a support structure; and
    a plurality of microplatforms, each microplatform having a top surface distally located from said support structure and at least one side surface, wherein at least one foreign biomolecule, including nucleic acids, is attached to each top surface and a transfectant reagent and cells in a cell growth media are added onto said support structure and onto each top surface such that at least one of the cells placed on each top surface become transfected with the at least one foreign biomolecule.

22. The cell transfection microplatform of claim 21, wherein said transfectant reagent is incubated for a period of time and then removed before the cells and the cell growth media are added onto said support structure and onto each top surface.

23. The cell transfection microplatform of claim 21, wherein said at least one side surface of each microplatform is treated with a non-binding compound.

24. The cell transfection microplatform of claim 21, wherein said at least one foreign biomolecule are attached at one time to the top surfaces.

25. The cell transfection microplatform of claim 21, wherein said at least one foreign biomolecule includes a DNA, RNA, or oligonucleotide.

26. The cell transfection microplatform of claim 21, wherein said transfected cells express at least one protein encoded by the at least one foreign biomolecule.

27. The cell transfection microplatform of claim 21, wherein said transfected cells incorporate a reporter gene used to confirm an expression of the at least one foreign biomolecule.

28. A method for making a cell transfection microplatform, said method comprising the steps of:

coating a top surface of a plate with a substantially thick layer of photoresist material;

exposing selected areas of the photoresist material to an ultraviolet light;

developing away unexposed areas of the photoresist material from the plate;

using a reactive ion etching process to form a plurality of microplatforms in the plate by etching away a predetermined amount of the top surface from the plate that is not covered by the exposed photoresist material; and removing the remaining exposed photoresist material from the plate which resembles the cell transfection microplatform.

29. The method of claim 28, further comprising the step of coating a side surface of each microplatform with a non-binding material.

30. The method of claim 28, wherein said cell transfection microplatform includes:

a support structure formed by the remaining top surface of the silica plate; and said plurality of microplatforms, each microplatform having a top surface distally located from said support structure and at least one side surface, wherein at least one foreign biomolecule, including nucleic acids, is attached to each top surface and a transfectant reagent and cells in a cell growth media are added onto said support structure and onto each top surface such that at least one of the cells placed on each top surface become transfected with the at least one foreign biomolecule.

31. A cell transfection plate, comprising:

a support structure having a top surface with at least one binding region and at least one non-binding region, wherein at least one foreign biomolecule, including nucleic acids, is attached to the at least one binding region and a transfectant reagent and cells in a cell growth media are placed on the top surface such that at least one of the cells adhered to the at least one binding region becomes transfected with the at least one foreign biomolecule.

32. The cell transfection plate of claim 31, wherein each foreign biomolecule is attached at one time to the at least one binding region.

33. The cell transfection plate of claim 31, wherein said at least one foreign biomolecule includes a DNA, RNA, or oligonucleotide.

34. The cell transfection plate of claim 31, wherein said transfection reagent is added, incubated and then removed before adding the cells and the cell growth media onto said top surface.

35. The cell transfection plate of claim 31, wherein said transfection reagent is mixed with said at least one foreign biomolecule.

36. The cell transfection plate of claim 31, wherein said transfection reagent is mixed with said cells and said cell growth media.

37. The cell transfection plate of claim 31, wherein said at least one non-binding region is coated with a non-binding compound.

38. The cell transfection plate of claim 37, wherein said non-binding compound includes nonionic hydrophilic molecules that have repeat units of polyethylene oxide with a terminal alkoxysilane.

39. The cell transfection plate of claim 31, wherein said transfected cells incorporate reporter genes used to confirm an expression of the at least one foreign biomolecule.

40. The cell transfection plate of claim 31, wherein said support structure is incorporated within a well of a multiwell plate.

* * * * *